(12) United States Patent
Schmidt et al.

(10) Patent No.: US 7,232,457 B2
(45) Date of Patent: Jun. 19, 2007

(54) FLUID WARMING CASSETTE WITH A TENSIONING ROD

(75) Inventors: Wayne Eugene Schmidt, Lakeville, MN (US); Scott Allen Entenman, St. Paul, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 605 days.

(21) Appl. No.: 10/214,966

(22) Filed: Aug. 8, 2002

(65) Prior Publication Data

US 2004/0026068 A1 Feb. 12, 2004

(51) Int. Cl.
*A61F 7/00* (2006.01)
*F28F 3/14* (2006.01)

(52) U.S. Cl. .................. 607/96; 607/104; 607/114; 165/46; 165/170

(58) Field of Classification Search ............ 165/46, 165/170; 62/530; 607/96, 108, 112, 114
See application file for complete search history.

(56) References Cited

U.S. PATENT DOCUMENTS

| | | | | |
|---|---|---|---|---|
| 419,745 | A * | 1/1890 | Adams | 383/43 |
| 670,029 | A * | 3/1901 | Meier | 383/43 |
| 768,945 | A * | 8/1904 | Kepler | 427/227 |
| 998,977 | A * | 7/1911 | Murray | 383/119 |
| 1,116,068 | A * | 11/1914 | Jackson | 383/43 |
| 1,139,370 | A * | 5/1915 | Putnam | 206/37.3 |
| 1,145,687 | A * | 7/1915 | Kepler | 383/119 |
| 1,185,695 | A * | 6/1916 | Marshall | 383/43 |
| 1,282,761 | A * | 10/1918 | Combes | 383/43 |
| 1,310,869 | A * | 7/1919 | Mchugh | 383/43 |
| 1,333,717 | A * | 3/1920 | Jackson, Jr. | 383/116 |
| 1,444,468 | A * | 2/1923 | Kinsey | 383/41 |
| 1,446,384 | A * | 2/1923 | Gilchrist | 383/43 |
| 2,041,190 | A * | 5/1936 | Kuhlke | 383/43 |
| 2,138,610 | A * | 11/1938 | Overly | 112/417 |
| 2,453,940 | A * | 11/1948 | Slobotkin | 383/43 |
| 2,567,602 | A * | 9/1951 | Higgins | 224/231 |
| 3,140,716 | A | 7/1964 | Harrison et al. | |
| 3,355,080 | A * | 11/1967 | Rausing et al. | 229/123.1 |

(Continued)

FOREIGN PATENT DOCUMENTS

EP 01 96 191 (A1) 5/1982

(Continued)

OTHER PUBLICATIONS

Brochure for "The Medi-Temp™ II GAYMAR™ Blood/Fluid Warmer", Gaymar Industries, Inc.

(Continued)

*Primary Examiner*—Leonard R. Leo
(74) *Attorney, Agent, or Firm*—Incaplaw;; Terrance A. Meador

(57) ABSTRACT

A fluid warming cassette for use in a fluid warming system includes a first sheet and second sheet joined with a flexed tensioning rod to form a fluid container with a periphery in which the flexed tensioning rod is disposed to tension the fluid container. The fluid container includes a fluid channel with inlet and outlet ports in fluid communication with the fluid channel. Preferably, the rod is flexed into an open-ended shape such as a "U" shape. So flexed, the rod tensions the fluid container, adding structural stability to the fluid warming cassette.

23 Claims, 7 Drawing Sheets

U.S. PATENT DOCUMENTS

| | | | |
|---|---|---|---|
| 3,485,245 A | 12/1969 | Lahr et al. | |
| 4,050,468 A * | 9/1977 | Wynnyk | 131/232 |
| 4,131,200 A | 12/1978 | Rinfret | |
| 4,602,910 A | 7/1986 | Larkin | |
| 4,707,587 A | 11/1987 | Greenblatt | |
| 4,731,072 A | 3/1988 | Aid | |
| 4,847,470 A * | 7/1989 | Bakke | 392/470 |
| 4,867,230 A * | 9/1989 | Voss | 165/46 |
| 4,919,134 A | 4/1990 | Streeter | |
| 4,919,326 A | 4/1990 | Deiger | |
| 5,098,202 A | 3/1992 | Rosenbaum | |
| 5,102,234 A | 4/1992 | Levy | |
| 5,205,348 A * | 4/1993 | Tousignant et al. | 165/46 |
| 5,245,693 A | 9/1993 | Ford et al. | |
| 5,381,510 A | 1/1995 | Ford et al. | |
| 5,384,923 A * | 1/1995 | Hwang et al. | 5/419 |
| 5,423,421 A | 6/1995 | Inoue et al. | |
| 5,520,975 A | 5/1996 | Inoue et al. | |
| 5,733,619 A | 3/1998 | Patel et al. | |
| 5,792,526 A | 8/1998 | Watanabe et al. | |
| 5,865,309 A | 2/1999 | Futagawa et al. | |
| 5,875,282 A | 2/1999 | Jordan et al. | |
| 6,464,666 B1 * | 10/2002 | Augustine et al. | 604/113 |
| 6,580,012 B1 * | 6/2003 | Augustine et al. | 602/42 |
| 6,673,098 B1 * | 1/2004 | Machold et al. | 607/96 |

FOREIGN PATENT DOCUMENTS

| | | | |
|---|---|---|---|
| EP | 0 119 469 | 2/1983 | |
| EP | 0 095 526 (A2) | 12/1983 | |
| EP | 1 459 777 A1 * | 9/2004 | 392/470 |
| JP | 2004-283573 A * | 10/2004 | 392/470 |

OTHER PUBLICATIONS

Search Report from PCT/US00/02630.
Written Opinion from PCT/US00/02630.

* cited by examiner

FLUID WARMING CASSETTE WITH A TENSIONING ROD

FIELD OF THE INVENTION

This invention is generally related to parenteral fluid warming systems and, more particularly, to the structure of a fluid warming cassette used with a warming apparatus, in which the structure of the cassette includes a fluid container with a tensioning rod.

BACKGROUND OF THE INVENTION

Fluid warming apparatuses, designed to warm and administer parentarel fluids and blood products (hereinafter "fluids"), are in common use. Generally, such fluids are heated and administered using fluid warming systems. A parenteral fluid warming system usually includes a warming unit into which a fluid warming cassette is placed. The fluid warming cassette includes a fluid container with a structure designed for handling and for being received and supported in the warming unit. The fluid container includes a fluid channel and is typically made of plastic film material and/or thin metal.

In use, the cassette is placed into the warming unit to heat the fluids as they flow through the fluid channel. Heat is transferred to the fluid through the fluid container from a heat source such as heated metal plates, heated liquid, or heated gas. Metal plate, "dry heat" exchanger warming units are widely known.

In such systems, heat transfer from the warming unit to the fluid warming cassette is typically by conduction, with the heat source including, for example, one or more metal plates brought into contact with the warming cassette. There are systems that operate by conduction between a bath of heated water and a fluid warming cassette. Still other systems operate by convection, disposing a fluid warming cassette in a flow of heated air. Those skilled in the art will appreciate that heat transfer in such systems is a complex process that actually compounds conduction, radiation, and convection. Therefore, characterization of a mode of heat transfer to a fluid warming cassette actually denotes the principal mode of transfer and does not necessarily exclude contribution by one or more additional modes.

To increase the thermal efficiency and temperature responsiveness of a fluid warming system in which a fluid warming cassette is disposed for conductive heat transfer from warming plates, the distance between the heater plates is usually very small. This implies that a fluid warming cassette should be a thin, flat container, constructed from selected materials. Plastic film materials are commonly used in the manufacture of disposable fluid warming containers. One such design is disclosed in U.S. patent application Ser. No. 09/415,558, entitled "PRESSURE TOLERANT PARENTERAL FLUID AND BLOOD CONTAINER FOR A WARMING CASSETTE", invented by Augustine et al., filed on Oct. 8, 1999, which is incorporated herein by this reference.

Since these fluid containers are thin, it would be difficult to insert one into a conductive warming unit simply by sliding it between the warming plates. The container may kink or tear when being slid into or out of such a small space. As a result, the fluid container needs some type of structural support, usually a frame. A frame adds rigidity to the fluid container so that the fluid warming cassette can be handled, and also inserted into and removed from the warming unit. Together, the fluid container and frame form a fluid warming cassette, a modular unit of equipment designed to be received in, or inserted into, a larger warming unit.

The frame of a fluid warming cassette comprehends numerous elements, including a handle portion that extends outside of the warming unit when the cassette is seated in the unit in order to provide something that can be grasped to manipulate the cassette for insertion and extraction. This type of construction adds steps to the process for manufacturing fluid warming cassettes, leading to higher manufacturing costs.

It would be advantageous if a simplified, effective, low cost fluid warming cassette could be developed for a "dry heat" parenteral fluid warming system in which the cassette is received between heating plates of a warming unit for conductive heat transfer therefrom.

It would be advantageous if a cassette fluid container could be invested with enough stiffness for insertion between close-set parallel warming plates of a warming unit, yet be thin enough to efficiently transfer heat by conduction from the plates to the fluid, without the requirement of an expensive frame.

It would be advantageous if the fluid warming cassette were provided with a keying mechanism that prevents it from being inserted either upside down, or backwards in a warming unit. It would further be advantageous if the cassette is provided with a stop that prevents the cassette from being inserted too far into the warming unit.

It would also be advantageous if the fluid warming cassette had a portion that extended outside the warming unit for convenient handling. It would further be advantageous if the extended portion and the keying mechanism of the fluid warming cassette were the same.

SUMMARY OF THE INVENTION

A fluid warming cassette useful in a system for warming parenteral fluids is provided. The cassette comprises a thermally conductive, flexible fluid container with a fluid channel, and a flexible tensioning rod or filament, or tensioning member, which imparts structural rigidity to the fluid container. The fluid container and rod may be joined into an integrated structure.

The tensioning rod is flexed into a shape with sides and at least one closed end, and the fluid container is disposed with respect to the flexed tensioning rod such that the fluid channel is within the shape defined by the flexed rod. The flexion of the rod urges the sides of the shape apart and against sides of the fluid container.

A portion of the rod forms a handle at an end of the cassette. The handle is for being grasped so that the cassette may be manipulated for insertion into and extraction from a warming unit.

Optionally, the warming cassette may be provided with a keying mechanism that prevents it from being inserted either upside down, or backwards in a warming unit. Portions of the rod may include elements of a keying mechanism. To key the cassette, the rod portions mate with corresponding elements in the warming unit. There may also me a stop that prevents the cassette from being inserted too far into the warming unit.

DETAILED DESCRIPTION OF THE INVENTION

This invention is a fluid warming cassette intended for use with a fluid warming unit to warm fluids for intravenous infusion. The cassette is designed for use with a "dry heat" warming unit in which heater plates are disposed in an opposing, spaced-apart configuration, separated by a thin laminar space. The cassette is received in the space between the heater plates, in close contact with the heater plates for transfer of heat by conduction from the plates to the cassette.

The fluid warming cassette includes a flexed tensioning rod, filament, or tensioning member and a fluid container. The fluid container is made of two or more sheets of thermally conductive plastic film material. The sheets of plastic film material are bonded or otherwise joined in a pattern which creates a fluid channel between the sheets. A fluid channel with a serpentine pattern is illustrated, although other patterns are contemplated. Preferably each of the plastic sheets is a film 0.004 in. (4 mil) thick, or less. The rod is flexed into a shape and assembled or joined with the sheets in a manner that tensions the fluid container, thereby imparting a rigidity to the fluid container, making it easy to handle and use.

Figure 1:
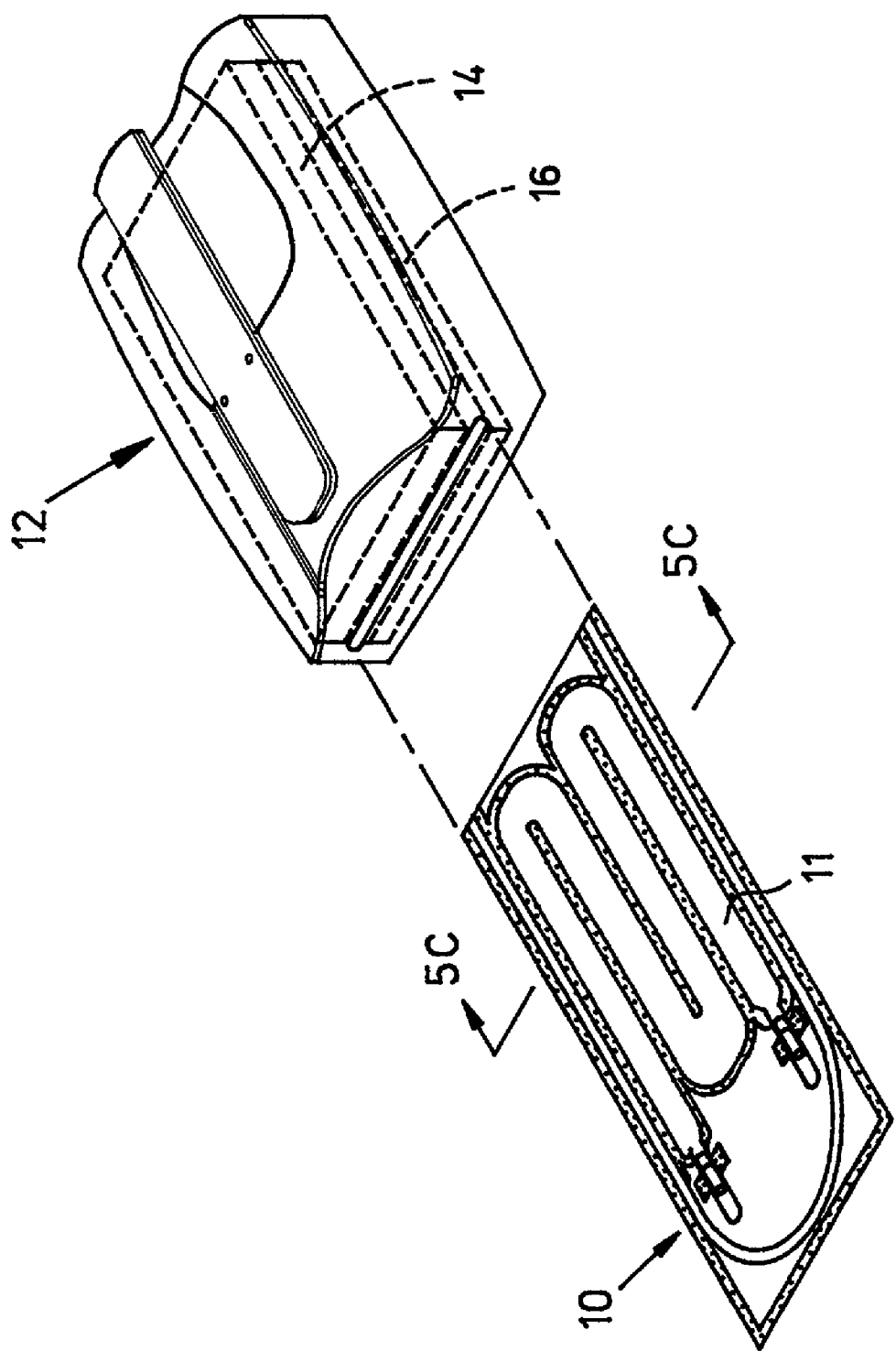
FIG. 1 is a perspective view of a fluid warming cassette according to this invention disposed for use with a fluid warming unit.

FIG. 1 is a perspective illustration of a fluid warming cassette 10 with a fluid channel 11 according to the invention for use with a fluid warming unit 12. The warming unit 12 is a "dry heat" unit with warming plates 14 and 16. The plates 14 and 16 are spaced apart at a fixed distance, and the cassette 10 is inserted between the plates 14 and 16 so that the fluid in the cassette 10 is heated by conduction from the plates 14 and 16 before infusion into a body. Alternately, the cassette could be warmed by convection in a stream of heated air, or by conduction in a bath of heated fluid.

Figure 2:
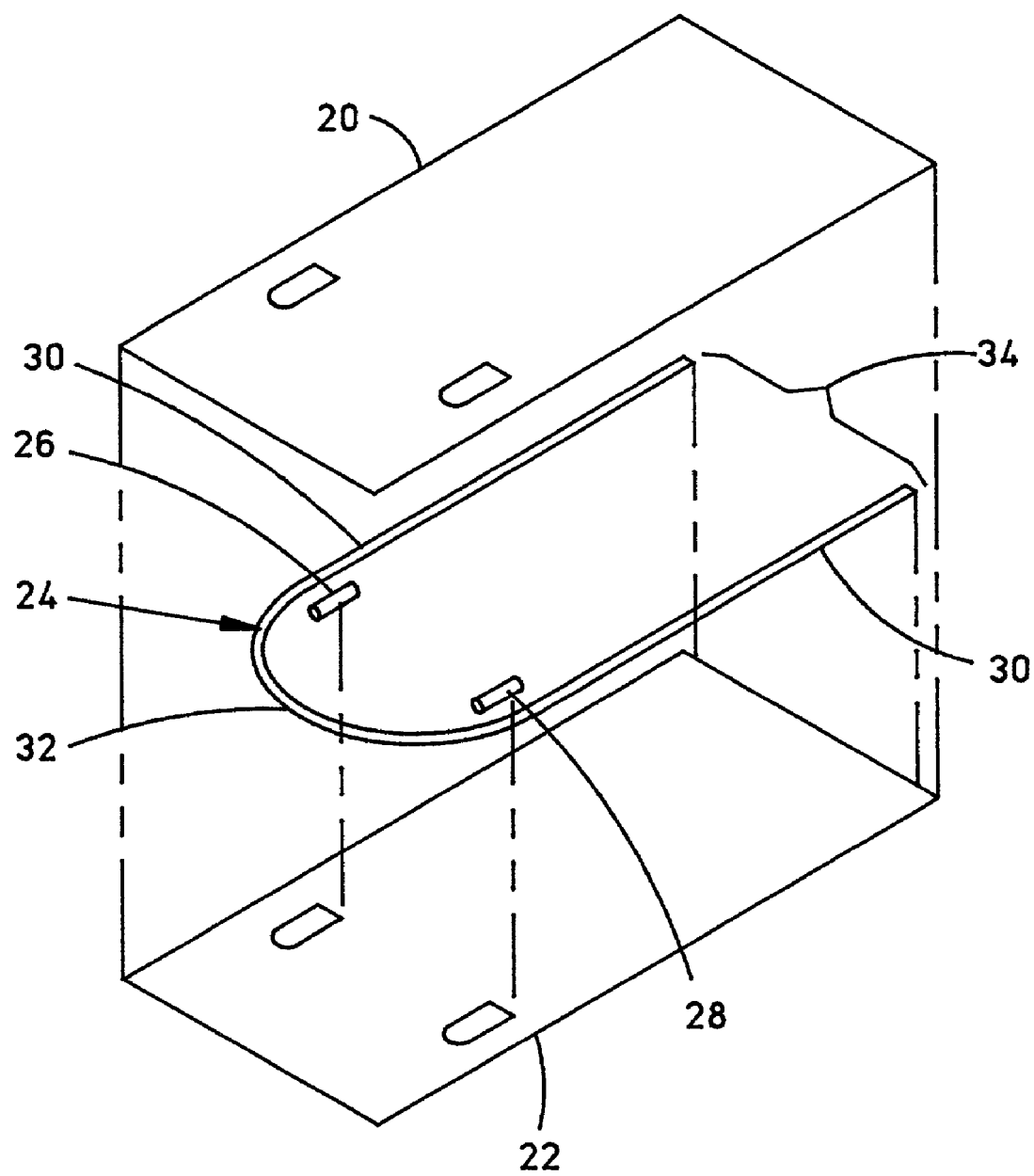
FIG. 2 is an exploded view of the fluid warming cassette of FIG. 1A.

FIG. 2 is an exploded view of the fluid warming cassette 10 of FIG. 1 showing its elements. The cassette 10 includes a first sheet 20, a second sheet 22, a flexed tensioning rod 24, an inlet port 26 and an outlet port 28. The rod 24 is a flexible filament, member or structure that has the shape of a thin, substantially straight piece when unflexed. During a process of making the cassette, the rod is flexed into a shape, preferably an open-ended shape with a closed end 32 that transitions to legs 30 which define an opposite open end 34. To assemble the cassette shown in FIGS. 1–3, the sheets 22, 24, the inlet 26 and outlet 28 ports are positioned in place to form a fluid container and the tensioning rod 24 is flexed to the desired shape and disposed between the sheets. A heat sealing platen, RF platen, or US horn is applied and the fluid container 40 is formed by joining the sheets in numerous places within and around their peripheries to form a periphery of the cassette including sides 34, distal end 36 and proximal end 38 (see FIG. 3). The legs 30 of the shape defined by the flexed rod are disposed near, within, or against the sides 34, and the closed end 32 is disposed near, within or against the proximal end 38. Between the legs 30, the first sheet 20 and second sheet 22 are fused or welded together in a fluid channel pattern to form the fluid channel 42. The inlet 26 and the outlet 28 are in fluid communication with the fluid channel 42.

Figure 3:
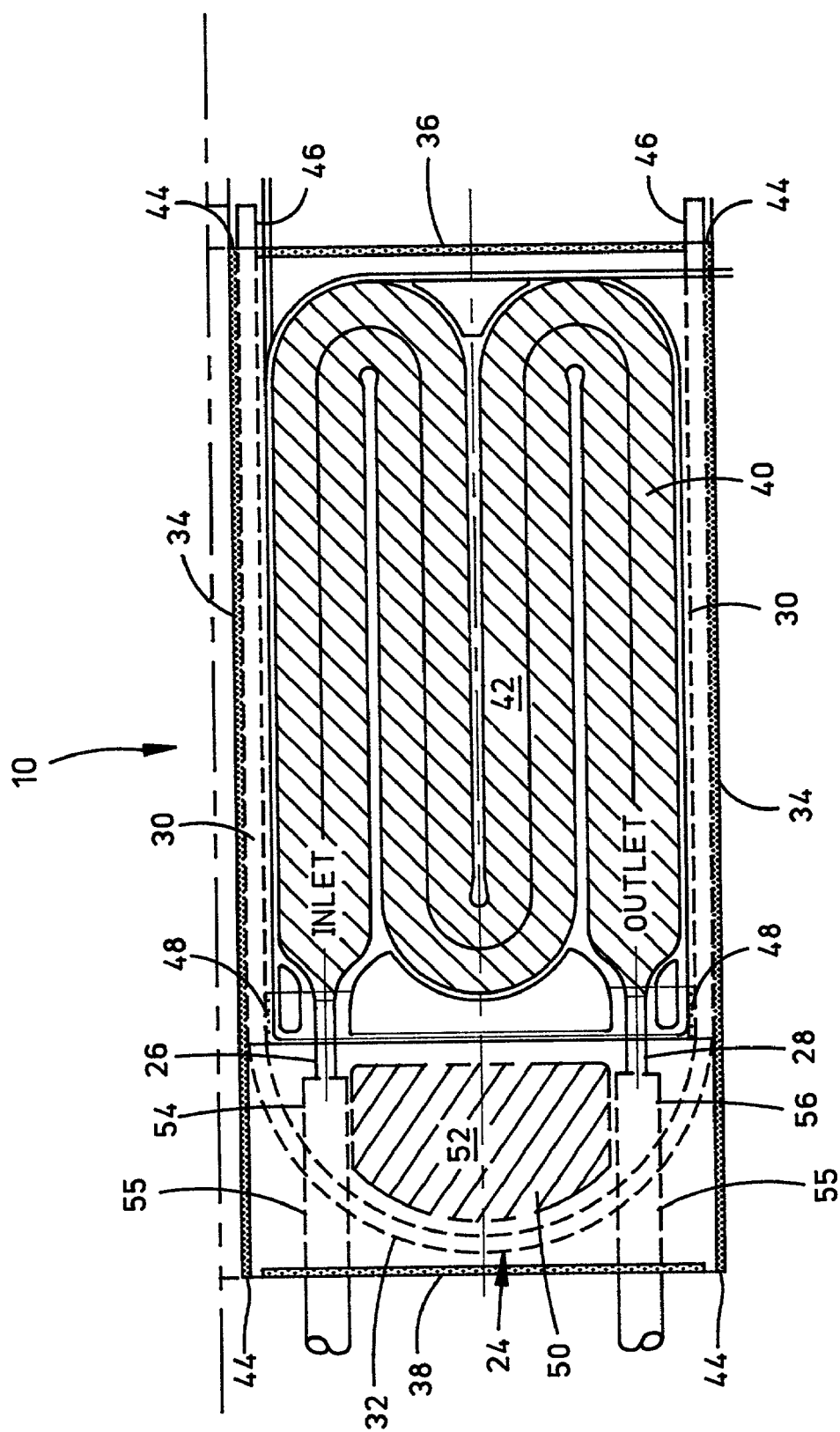
FIG. 3 is a more detailed depiction of the fluid warming cassette of FIG. 1A.

FIG. 3 shows a top view of the cassette 10 assembled as illustrated in FIG. 2. The rod 24 tensions or stiffens the fluid container 40 within a single plane represented by orthogonal X and Y axes. The X and Y axes are referred to herein as first and second directions, respectively. Likewise, the fluid container 40, which is substantially planar, or flat, is disposed in a flat or laminar space containing the illustrated portion of the single plane.

As FIGS. 1–3 illustrate, the tensioning rod 24 is in the open-ended shape of a planar figure. The flexion of the rod and the shape are intended to impart tension to the fluid container when the flexed rod and sheets are joined together. In this instance a "U" shaped figure is used for ease of explanation. In the "U" shape, the legs may be disposed in a substantially parallel relationship or may converge or diverge at a shallow angle. Use of the "U" shape in this specification is for illustration only, and is not intended to foreclose use of other shapes such as the "C", the "V", and other equivalent shapes.

Referring again to FIG. 3, the tensioning rod 24 is flexed into, and held in, the "U" shape, which comprises legs 30 extending from the closed end 32. In the illustrative example, the legs 30 are substantially parallel (that is, altogether parallel, or converging or diverging at a shallow angle) and the closed end 32 has a curved or arcuate shape, for example, that of a semicircle. The tensioning rod 24 has a spring-like mechanical property that urges the legs 30 outwardly, away from each other, when the rod is flexed into the shape. This is similar to a bow that is bent to receive an arrow. Each end of the bow is subject to a force tending to move it away from the other, but is restrained from such movement by the string, making the string taut. In this case, the legs 30 are subject to forces tending to move them away from each other; but the legs are restrained from such movement by the bonded sheets along sides 34. This tautens the fluid container between the legs 30, stiffening the fluid warming cassette 10 so that it may be handled, manipulated, or otherwise used or processed as a single modular unit.

Those skilled in the art will appreciate that the rod need not be disposed precisely between the sheets which compose the fluid container, so long as it is flexed and then joined, while still flexed, to the fluid container in a manner that urges flexed portions of itself, or otherwise acts against the periphery of the container so as to impart stiffness to the container.

As discussed earlier, the cassette 10 has a periphery including opposing sides 34, a distal end 36 and a proximal end 38. The tensioning rod 24 is flexed into the desired open-ended shape and joined with sheets 20 and 22, which are bonded, or otherwise permanently joined or connected, around along the periphery. The bonds can either be complete or have gaps. Alternatively, the peripheral bonds could include just the sides 34 or in combination with ends 36 and 38. Shown in FIG. 3, the bonds are not complete, there are small gaps 44 near the corners. The figure also shows that an end portion 46 of each of the legs 30 extends outside the distal end 36 through gaps 44. In one embodiment, the end portions 46 act as stops when the cassette 10 is inserted fully into the warmer 12. Other types of stops may also be used. As a consequence of bonding, joining, or connecting, the tensioning rod 24 cannot be separated from the fluid container once the cassette is assembled. In addition, the tensioning rod 24 may be further retained in place by additional bonds 48 of the sheets near the inlet 26 and outlet 28. As best seen in FIG. 3, the legs 30 provide stiffness in the first direction (X-axis). The closed end 32 of the tensioning rod 24 near the proximal end 38, and the tension force of the legs 30 trying to separate makes the sheets 20 and 22 tauten the cassette in the second direction (Y-axis). Taken together, the cassette has stiffness generally in the X-Y plane.

The proximal end 38 provides a handle portion 50 of the fluid warming cassette. The handle portion 50 is generally the area contained inside the semicircular closed end 32 and extending away from the fluid container 40 which may accommodate finger purchase. When the cassette 10 is engaged with warming device 12 (see FIG. 1), the handle portion 50 is not received (at least, not entirely received) between the plates 14 and 16. The handle portion 50 remains accessible while the rest of the cassette is being heated between plates 14 and 16.

The handle portion may include a label surface area 52 which may be used for labeling (see FIG. 3). Since the majority of the cassette 10 is inside the warming unit during use, it is convenient to have labeling visible to the user even during use. Handle portion 50 is always external to the warming unit and, therefore, is an ideal platform for such labeling. In addition, the handle portion 50 may include a mechanism for supporting fluid inlet and fluid outlet tubing, and providing strain relief preventing undue tension being applied to the tubing. Without this kind of strain relief, there is the risk of tension on the tubing, resulting in tearing the plastic film material. Attaching the tubes helps to prevent kinking of the tubing as it leaves the warming unit.

The rod 24 may be a filament formed from a material selected from the group consisting of polyolefin, polyethylene, polypropylene, polyvinyl chloride (PVC), polyurethane, and ethyl vinyl acetate (EVA) co-polymer. Other suitable rod materials include spring steel, aluminum, and any suitable metal capable of providing the appropriate tension. In addition, composite materials may be used for the rod 24. For example, the rod 24 may be similar in construction to a composite fishing pole, made from fiberglass or other composite materials capable of providing the appropriate tension. The rod 24 can be manufactured by extrusion, die cutting, injection molding, thermal processes or other processes compatible with the materials selected. Many different cross-sectional shapes are contemplated for the rod 24 including circular, oval, rectangular, I-beam, tubular and other shapes. Shown in the figures is a circular cross-section, which should not be limiting.

The first sheet 20 and second sheet 22 which are joined to form the fluid container 40 may be made from one or more materials selected from the group consisting of polyester, polyamide (Nylon®, DuPont), polyethylene glycol terephthalate (Mylar®, DuPont), metal foils, ionomer resins (Surlyn®, DuPont), polyolefin, polyethylene, polypropylene, polyvinyl chloride (PVC), polyurethane, and ethyl vinyl acetate (EVA) co-polymer.

The fluid container 40 includes the fluid channel 42 and at least a first port 26 for fluid communication with the fluid channel 42, which is highlighted with cross-hatched lines in FIG. 3. When the fluid warming cassette is deployed for use, a first tube 54 is joined to the first port 26. Optionally, the first tube may be attached 55 to the cassette near the handle portion 50. The fluid container 40 also includes a second port 28 in fluid communication with the fluid channel 42. A second tube 56 is joined to the second port 28.

Figure 4:
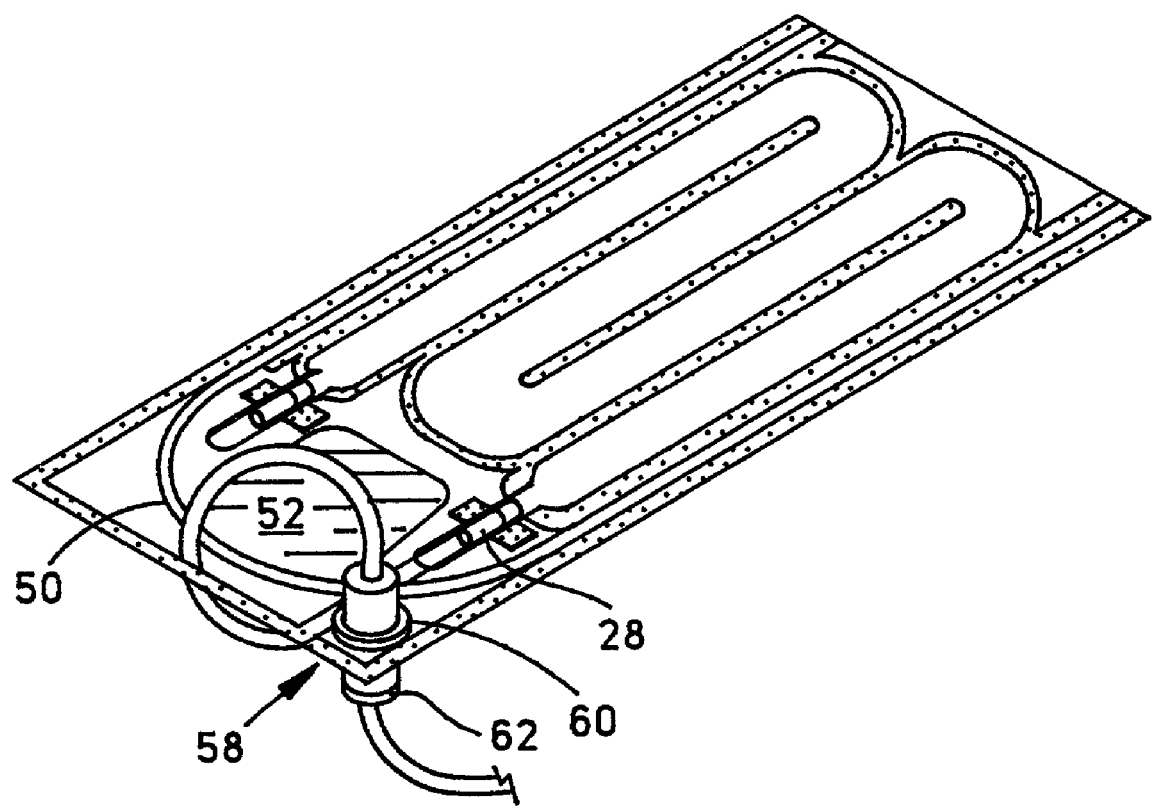
FIG. 4 illustrates the fluid warming cassette 10 of FIG. 1A, detailing an optional bubble trap feature.

FIG. 4 illustrates the warming cassette 10 of FIG. 1, detailing an optional bubble trap feature. The warming cassette 10 optionally includes a bubble trap 58 attached to the handle portion 50 for support. The bubble trap 58 traps any air bubbles that may have inadvertently been introduced into the inlet tubing from the IV bag or may have been created by "out-gassing" during the warming of the fluids. The bubble trap 58 has an input 60 connected to the second port 28. The bubble trap 58 has an output 62 to supply fluid, and a gas exhaust port (not shown) to vent gases escaping from the communicated fluid. The output 62 is operatively connected to the patient's IV catheter (not shown).

The bubble trap 58 can be mechanically attached or bonded through thermal, adhesive, or chemical means to the handle portion 50. Attaching the bubble trap 58 to the handle portion 50 makes it less likely that the trap 58, or its associated tubing will be inadvertently disconnected from the cassette 10.

As discussed, the handle portion 50 may include a label surface area 52, highlighted with cross-hatched lines in FIG. 4. In the preferred embodiment, labeling may be printed directly on the label surface area 52, eliminating the need for a separate label. In addition, labeling may be printed anywhere in the upper or lower sheets and may be printed before, or after, the sheets are attached together. In another embodiment, the cassette 10 may receive a label (not shown) overlying the label surface are 56. The label can be visible to the eye, or configured for electronic identification, such as a bar code.

Figure 5A:
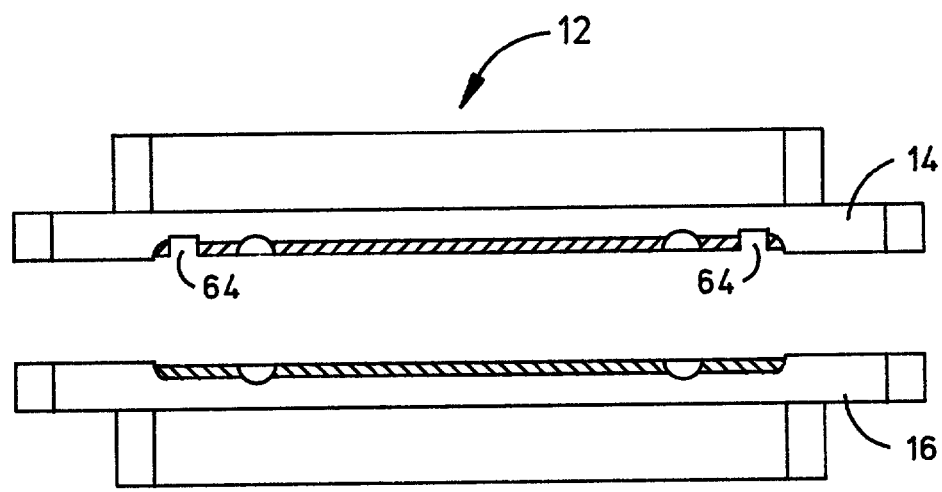
FIGS. 5A through 5C illustrate details of an optional keying mechanism used to selectively orient the fluid warming cassette in the fluid warming unit.
Figure 5B:
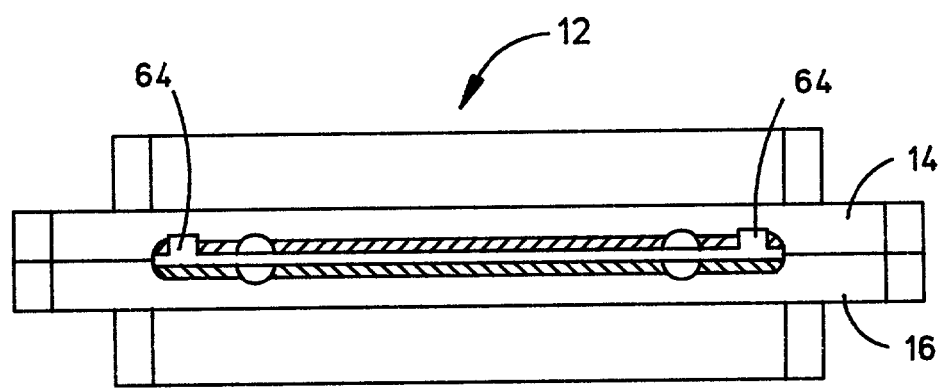
Figure 5C:
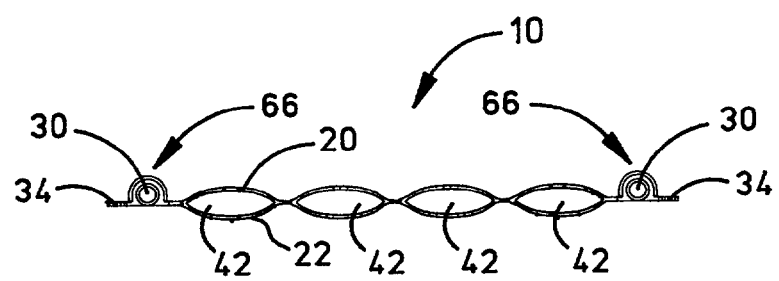

FIGS. 5A through 5C illustrate elements of an optional keying mechanism used to orient the cassette 10 in the warming unit 12. The warming unit 12 includes the first and second opposing warming plates 14 and 16, adapted to accept the warming cassette 10 in a first orientation. FIG. 5A is a simplified end view of the warming unit 12. The warming plates 14 and 16 have been separated for the purpose of clarifying the optional keying mechanism. Two grooves 64 are formed in the upper plate 14 to cooperate with the elements of the keying mechanism on the fluid warming cassette 10. FIG. 5B illustrates the warming unit 12 with the warming plates 14 and 16 assembled for normal operation.

Figure 6A:
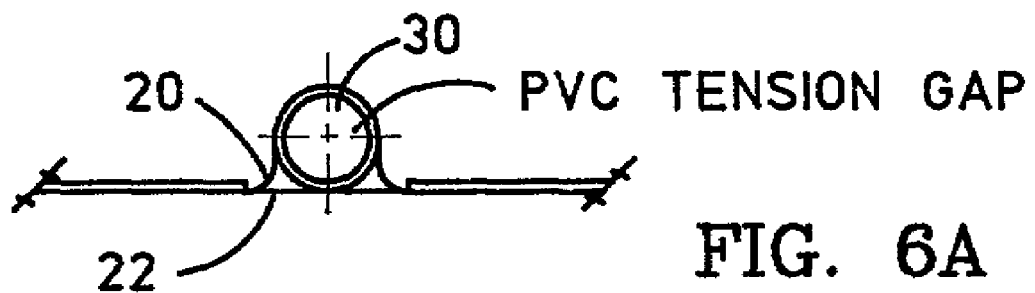
FIGS. 6A through 6C illustrate details of the flexed tensioning rod in the fluid warming cassette.
Figure 6B:
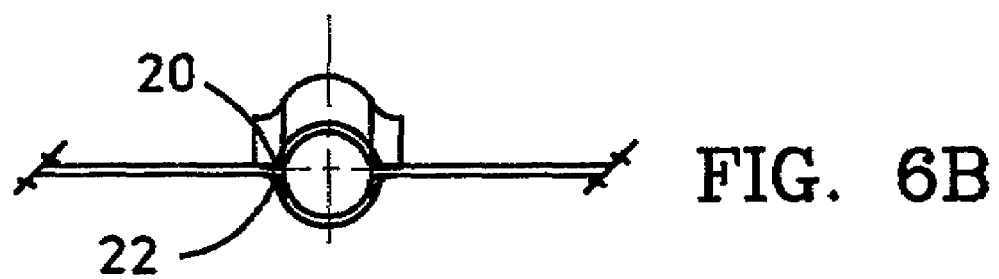
Figure 6C:
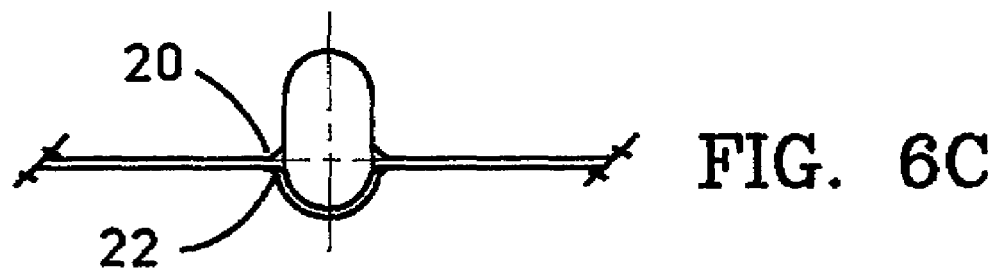

FIG. 5C is a sectional view taken along 5C—5C of FIG. 1. These figures illustrate an embodiment of the fluid warming cassette in which the legs 30 are positioned within the cassette 20 to act as a keying mechanism 66 with the grooves 64 to mate the cassette 10 with the warming plates in a predetermined orientation. FIGS. 6A–6C show elements of the keying mechanism. In FIG. 6A, the rod 24 is captured between first sheet 20 and second sheet 22 in such a way that a raised key 66 is formed. In FIG. 6B, the rod is deformed/formed upward to form a raised key 66. In FIG. 6C, the rod is oval in cross section and the legs 30 are captured between first sheet 20 and second sheet 22 in such a way forming a raised key 66. When the warming cassette 10 is received between the plates 14 and 16, the cassette 10 can be inserted or slid into the space between the plates only if the keys 66 are received in the grooves 64. Otherwise, the keys 66 will prevent the cassette from being inserted into the warming unit 12 between the plates 14 and 16.

The cassette 10 may also include a stop mechanism. In one embodiment, the distal ends 46 of the legs 30 extend beyond the distal end 36 of the cassette 10. When the cassette 10 is fully received between the plates 14 and 16, the distal ends 46 make contact and stop the cassette from being inserted any further between the plates 14 and 16. Other stop embodiments may be incorporated into the design, such as ridges that are formed or affixed to the cassette like that would stop the cassette when the ridge hit the warming plates.

Figure 7:
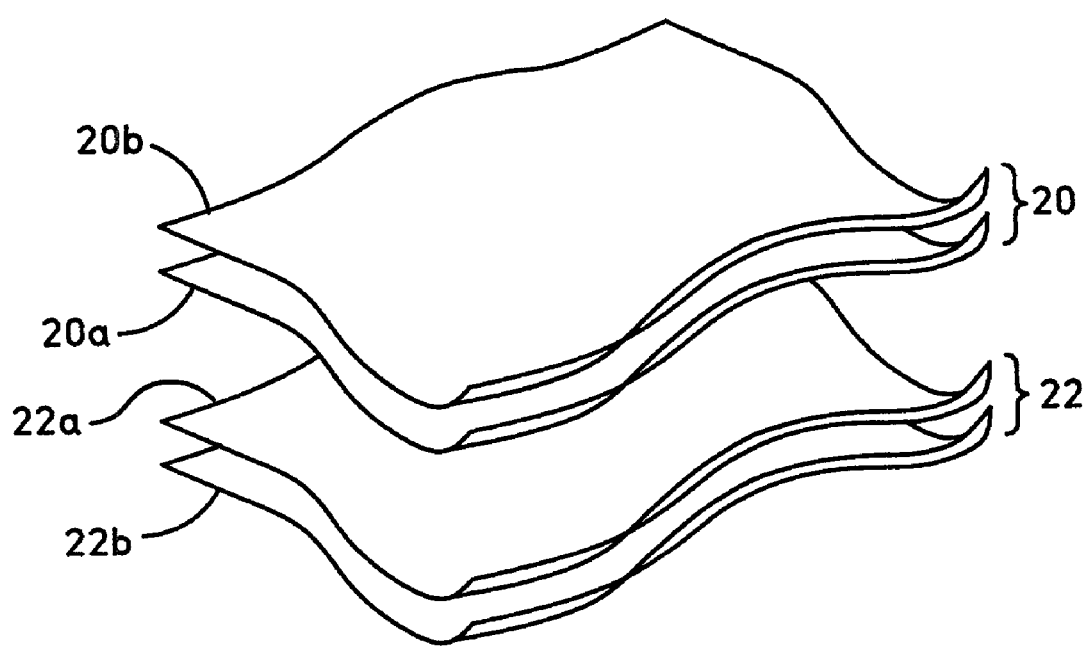
FIG. 7 illustrates a multi-layer construction for first and second sheets of the fluid container.

In some cases, a multi-layer construction provides advantages such as tailoring the sheets of which the fluid container is formed for optimum strength so that the container can accommodate substantial fluid pressures, such as those encountered with use of an IV pump. A multi-layer construction is disclosed in applicants U.S. patent application Ser. No. 09/415,558 filed on Oct. 8, 1999, which is incorporated in its entirety by this reference. In an alternative construction, the first sheet 20 or the second sheet 22, or both, may have a multi-layer construction. As shown in FIG. 7, each sheet could include an inner thermo-sealable layer 20a, 22a and a outer structural layer 20b, 22b. The thermo-sealable layer may be selected from the group of materials consisting of polyester, polyamide (Nylon®, DuPont), polyethylene glycol terephthalate (Mylar®, DuPont), metal foils, and ionomer resins (Surlyn®, DuPont). The outer structural layer may be selected from the group of materials consisting of polyolefin, polyethylene, polypropylene, polyvinyl chloride (PVC), polyurethane, and ethyl vinyl acetate (EVA) co-polymer. Many techniques are contemplated for bonding the layers of a multi-layered sheet to create a laminated structure. These include adhesive bonding the layers, thermal bonding the layers and extruding a molten layer of one material directly onto a layer of another material layer ("extrusion coating").

Referring again to FIG. 7. The first sheet 20 is shown, including a plurality of flexible film layers; two layers 20a and 22b of the first sheet shown. The second sheet 22 includes a plurality of layers, with layers 22a and 22b of the second sheet being shown. A construction of the warming cassette 10 with multi-layer sheets is similar to previously disclosed with reference to FIG. 2. The first and bottom multi-layered sheets 20, 22 are positioned so that the thermo-sealable layers 20a, 22a are in opposition to and face each other. The rod 24 is flexed into the desired shape and positioned between the multi-layered sheets along with inlet 26 and outlet 28 ports. A heat sealing platen, RF platen, or US horn is applied to one or both of the outside structural layers 20b, 22b at a temperature which is above the melting point of the material of thermo-sealable layers, but below the melting point of the material of the structural layers, joining the multi-layer sheets together. The pressure tolerance of the fluid container 40 may be selectively tailored by using multiple-layer sheets.

In another embodiment, the top 20 and bottom 22 sheets are constructed using materials with a low coefficient of friction. In a multi-layer sheet design, the outside layers 20b, 22b of sheets 20 and 22, respectively are constructed using materials with a low coefficient of friction. The lower coefficient of friction of permits the fluid warming cassette 10 to be more easily inserted between warming plates 14 and 16 (see FIG. 1).

The fluid warming cassette 10 can be inserted into the warming unit 12 by a user grasping the integral handle portion 50, orienting the warming cassette 10 so that the keys 66 are aligned with the grooves 64, inserting the distal end 36 between the plates 14 and 16 and sliding the warming cassette 10 inwardly between the plates 14 and 16 until the stopping mechanism 46 halts further insertion.

Other variations and embodiments of the prevent invention will occur to those skilled in the art with reflection upon the disclosed examples of the present invention cassette fluid container and formation of such a cassette fluid container.

We claim:

1. A system for warming parenteral fluids, comprising:
a fluid warming unit with spaced-apart warming plates; and
a fluid warming cassette for being slid between the spaced-apart warming plates, the cassette including:
a first sheet and a second sheet joined together by a pattern of bonding defining a fluid container with a periphery, the periphery having a proximal end, a distal end and first and second sides therebetween;
the first sheet including a plurality of layers and the second sheet including a plurality of layers;
the pattern of bonding further defining a fluid channel in the fluid container;
the fluid channel having a serpentine shape;
first and second ports in fluid communication with the fluid channel;
a rod flexed into a "U" shape, the "U" shape having first and second legs joined by a closed, curved end, and an opposite open end, the closed end being positioned near the proximal end and the open end being positioned near the distal end;
the first and second legs positioned inside and along the first and second sides of the periphery;
the fluid channel disposed between the first and second legs;
the "U" shape tensioning the fluid container within a plane; and,
a handle portion in the proximal end including the closed, curved end.

2. The system of claim 1, the fluid warming cassette further including a keying mechanism.

3. The system of claim 2 in which the distal end includes an insertion stop.

4. The system of claim 3 in which the first and second legs include ends proximate the open end, and the insertion stop includes the ends.

5. The system of claim 1, the fluid warming cassette further including a bubble trap attached to the handle portion, the bubble trap having an input connected to the second port, and an output for supplying fluid.

6. The system of claim 1, in which the handle portion includes a label surface.

7. The system of claim 1 in which the first sheet further includes a label.

8. A fluid warming cassette, comprising:
a first sheet and a second sheet joined together to form a fluid container with a periphery, the periphery having a proximal end, a distal end and first and second sides therebetween;
a rod flexed into an open-ended "U" shape and disposed between the first sheet and second sheet, inside the periphery;
the "U" shape tensioning the fluid container within a plane;
the "U" shape having first and second legs joined by a closed, curved end, and an opposite open end, the closed end being positioned near the proximal end and the open end being positioned near the distal end;
the first and second legs being positioned inside and along the first and second sides of the periphery;
a fluid channel in the fluid container, the fluid channel having a serpentine shape disposed between the first and second legs;
first and second ports in fluid communication with the fluid channel;

a handle portion at the proximal end including the closed, curved end; and a bubble trap attached to the handle portion, the bubble trap having an input connected to the second port, and an output.

9. The fluid warming cassette of claim 8 further comprising means for orienting the fluid warming cassette with a warming unit.

10. The fluid warming cassette of claim 8 further comprising means for stopping the fluid warming cassette while being inserted in a warming unit.

11. The fluid warming cassette of claim 8 in which the rod is made from a material selected from the group consisting of polyvinyl chloride (PVC), polyurethane, polyolefin, polypropylene, polyethylene, polyester, ethyl vinyl acetate (EVA), and other polymeric materials.

12. The fluid warming cassette of claim 11 in which the rod is formed by extrusion.

13. The fluid warming cassette of claim 11 in which the rod is formed by a thermo-process.

14. The fluid warming cassette of claim 8 in which the rod is made from a material selected from the group consisting of spring steel, aluminum, and other metallic materials.

15. The fluid warming cassette of claim 8 in which the rod is made from a composite material.

16. The fluid warming cassette of claim 8 in which the rod is circular in cross-section.

17. The fluid warming cassette of claim 8 in which the rod is oval in cross-section.

18. The fluid warming cassette of claim 8 in which the first sheet includes an inner layer and an outer layer laminated to the inner layer; and in which the second sheet includes an inner layer and an outer layer laminated to the inner layer.

19. The fluid warming cassette of claim 18 in which the inner layers of the first and second sheets are formed from a first material having a first melting point, and the outer layers of the first and second sheets are formed from a second material having a second melting point which is lower than the first melting point.

20. The fluid warming cassette of claim 18 in which the inner layers of the first and second sheets are joined by a thermo-bond.

21. The fluid warming cassette of claim 18 in which first and second sheets are formed by extrusion coating.

22. The fluid warming cassette of claim 18 in which the inner layer material is selected from the group of materials consisting of polyester, polyamide, polyethylene glycol terephthalate, metal foils, and ionomer resins.

23. The fluid warming cassette of claim 18 in which the outer layer material is selected from the group of materials consisting of polyolefin, polyethylene, polypropylene, polyvinyl chloride (PVC), polyurethane, and ethyl vinyl acetate (EVA) co-polymer.

* * * * *